United States Patent
Bossoutrot et al.

(10) Patent No.: US 8,809,601 B2
(45) Date of Patent: *Aug. 19, 2014

(54) METHOD FOR PREPARING OLEFIN FLUORINE COMPOUNDS

(75) Inventors: Jean-Michel Bossoutrot, Chaponost (FR); Pierre-Marie Sedat, Fleurieux sur l'Arbresle (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,256

(22) PCT Filed: May 19, 2010

(86) PCT No.: PCT/FR2010/050970
§ 371 (c)(1),
(2), (4) Date: Jan. 19, 2012

(87) PCT Pub. No.: WO2011/010023
PCT Pub. Date: Jan. 27, 2011

(65) Prior Publication Data
US 2012/0116133 A1 May 10, 2012

(30) Foreign Application Priority Data
Jul. 23, 2009 (FR) ...................................... 09 55137

(51) Int. Cl.
*C07C 17/25* (2006.01)

(52) U.S. Cl.
USPC .......................................... 570/155; 570/226

(58) Field of Classification Search
None
See application file for complete search history.

(56) References Cited

U.S. PATENT DOCUMENTS 4,414,185 A * 11/1983 Harrison ........................ 423/163
6,548,719 B1 4/2003 Nair et al.

(Continued)

FOREIGN PATENT DOCUMENTS

| JP | 2004018308 | 1/2004 |
| SU | 0 709 537 | 1/1980 |

(Continued)

OTHER PUBLICATIONS

Knunyants, I.L., et al. XP 000578879—Reactions of Fluoro Olefins—Communication 13—Catalytic Hydrogenation of Perfluoro Olefins. pp. 1312-1317 Academy of Sciences of the USSR.

(Continued)

*Primary Examiner* — Fereydoun G Sajjadi
*Assistant Examiner* — Medhanit Bahta
(74) *Attorney, Agent, or Firm* — Brinks Gilson & Lione

(57) ABSTRACT

The invention relates to a method for preparing olefin fluorine compounds. Specifically, the invention relates to a method for producing a (hydro)fluoroolefin compound, including: (i) in an agitated reactor provided with at least one reactant inlet and at least one outlet, contacting, with potassium hydroxide in an aqueous reaction medium, at least one compound containing three to six carbon atoms, at least two fluorine atoms, and at least one hydrogen atom, with the proviso that at least one hydrogen atom and one fluorine atom are located on adjacent carbon atoms, so as produce the (hydro)fluoroolefin compound, separated in a gaseous state from the reaction medium and from potassium fluoride; (ii) in an aqueous medium, contacting the potassium fluoride formed in step (i) with calcium hydroxide in a second reactor so as to produce potassium hydroxide and to precipitate calcium fluoride; (iii) separating the calcium fluoride precipitated in step (ii) from the reaction medium; and (iv) optionally recirculating the reaction medium after optionally recirculating the reaction medium after optionally adjusting the concentration of potassium hydroxide in step (i), characterized in that potassium hydroxide, with regard to the reaction medium of step (ii), is between 10 and 35 wt % of the weight of the water/potassium hydroxide mixture of the medium.

18 Claims, 1 Drawing Sheet

(56) References Cited

U.S. PATENT DOCUMENTS

| 2010/0121115 A1 | 5/2010 | Rao et al. |
| 2010/0145111 A1 | 6/2010 | Sharratt et al. |
| 2010/0185029 A1 | 7/2010 | El Sheikh et al. |

FOREIGN PATENT DOCUMENTS

| WO | 03/027051 | 4/2003 |
| WO | 2007/056194 | 5/2007 |
| WO | 2007/144665 | 12/2007 |
| WO | WO 2008/030439 A2 | 3/2008 |
| WO | WO 2008/030440 A2 | 3/2008 |
| WO | WO 2008/075017 A2 | 6/2008 |
| WO | WO 2008075017 A2 * | 6/2008 |
| WO | WO2009/003157 A1 | 12/2008 |
| WO | 2009/138764 | 11/2009 |

OTHER PUBLICATIONS

Sianesi, Dario XP009092725 Fluoroolefine—Nota I. Cis e trans 1,2,3,3,3-Pentafluoropropilence pp. 850-861.
Nouveau Traite De Chimie Minerale—Public Sous La Direction De-Paul Pascal—Tome II—Deuxieme Fascicule—Masson Et Cie, Editeurs 1963.
WPI Thompson—XP-002568903—Thompson Scientific, London GB; AN—1980-61936C-Lopatkina.
International Search Report for PCT/FR2010/050043, dated Apr. 13, 2010.
Office Action dated Oct. 22, 2013 for U.S. Appl. No. 13/144,239.

* cited by examiner

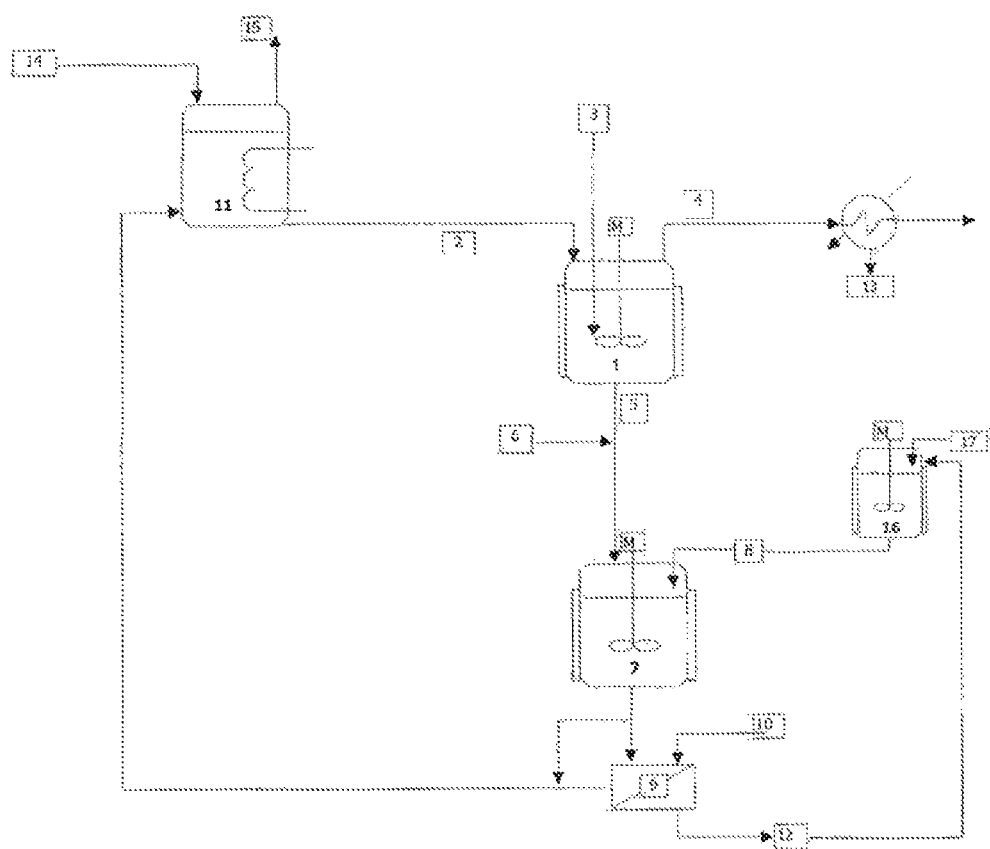

METHOD FOR PREPARING OLEFIN FLUORINE COMPOUNDS

FIELD OF THE INVENTION

A subject-matter of the invention is a process for the preparation of fluoroolefin compounds. The invention relates more particularly to a process for the preparation of hydrofluoropropenes.

TECHNOLOGICAL BACKGROUND

Hydrofluorocarbons (HFCs) and in particular hydrofluoroolefins (HFOs), such as 2,3,3,3-tetrafluoro-1-propene (HFO-1234yf), are compounds known for their properties of refrigerants and heat-exchange fluids, extinguishers, propellants, foaming agents, blowing agents, gaseous dielectrics, monomer or polymerization medium, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

1,2,3,3,3-Pentafluoropropene (HFO-1225ye) is a synthetic intermediate in the manufacture of 2,3,3,3-tetrafluoro-1-propene (HFO-1234yf).

The majority of the processes for the manufacture of hydrofluoroolefins involve a dehydrohalogenation reaction. Thus, the document WO 03/027051 describes a process for the manufacture of fluoroolefins of formula $CF_3CY=CX_nH_p$, in which X and Y each represent a hydrogen atom or a halogen atom chosen from fluorine, chlorine, bromine or iodine and n and p are integers and can independently take the value zero, 1 or 2, provided that (n+p)=2, which comprises bringing a compound of formula $CF_3C(R^1_aR^2_b)C(R^3_cR^4_d)$, with $R^1$, $R^2$, $R^3$ and $R^4$ independently representing a hydrogen atom or a halogen atom chosen from fluorine, chlorine, bromine or iodine, provided that at least one of $R^1$, $R^2$, $R^3$ and $R^4$ is a halogen atom and that at least one hydrogen atom and one halogen atom are situated on adjacent carbon atoms, a and b being able independently to take the value zero, 1 or 2, provided that (a+b)=2, and c and d being able independently to take the value zero, 1, 2 or 3, provided that (c+d)=3, into contact with at least one alkali metal hydroxide in the presence of a phase transfer catalyst.

This document teaches, in Example 2, that, in the absence of a phase transfer catalyst, there is no reaction when 1,1,1,3,3-pentafluoropropane (HFC-245fa) is brought into contact with a 50% by weight aqueous potassium hydroxide (KOH) solution at ambient temperature and under pressure for 24 hours.

In addition, this document teaches a reaction temperature of between −20° C. and 80° C.

The document WO 2008/075017 illustrates the dehydrofluorination reaction of 1,1,1,2,3,3-hexafluoropropane (HFC-236ea) to give 1,2,3,3,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (Test 1). In the presence of a phase transfer catalyst, this conversion is achieved after only 2.5 hours and the selectivity is virtually unchanged (Test 4). As indicated in Table 2 of this document, it is necessary to use an organic solvent in order to increase the selectivity for HFO-1225ye.

WO 2007/056194 describes the preparation of HFO-1234yf by dehydrofluorination of 1,1,1,2,3-pentafluoropropane (HFC-245eb) either with an aqueous KOH solution or in the gas phase in the presence of a catalyst, in particular over a catalyst based on nickel, carbon or a combination of these.

The document Knunyants et al., Journal of the USSR Academy of Sciences, Chemistry Department, "Reactions of fluoro-olefins", Report 13, "Catalytic hydrogenation of perfluoro-olefins", 1960, clearly describes various chemical reactions on fluorinated compounds. This document describes the dehydrofluorination of 1,1,1,2,3,3-hexafluoropropane (236ea) by passing through a suspension of KOH powder in dibutyl ether, to produce 1,2,3,3,3-pentafluoro-1-propene (HFO-1225ye) with a yield of only 60%. This document also describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether with a yield of only 70%.

Furthermore, FIG. 2 on page 51 of Part 2 of the nouveau traité de chimie minerale [New Treatise on Inorganic Chemistry] by P. Pascal, Ed. 1963, shows the appearance of the liquid/solid equilibria of the water and potassium hydroxide system and the measurements are collated in the table on page 52.

The dehydrofluorination reactions as described above result, in addition to the desired hydrofluoroolefin compound, in the formation of water and potassium fluoride. Furthermore, the implementation of such a reaction continuously is not easy on the industrial scale as at least three phases (gas, liquid and solid) are involved.

BRIEF DESCRIPTIONS OF THE DRAWINGS

FIG. 1 is a schematic of a process in accordance with the present invention,

DETAILED DESCRIPTION OF THE INVENTION

The present invention provides a process for the continuous or semicontinuous manufacture of a (hydro)fluoroolefin compound which makes it possible to overcome the abovementioned disadvantages. A subject-matter of the present invention is thus a process for the continuous or semicontinuous manufacture of a (hydro)fluoroolefin compound comprising (i) bringing at least one compound comprising from three to six carbon atoms, at least two fluorine atoms and at least one hydrogen atom, provided that at least one hydrogen atom and one fluorine atom are situated on adjacent carbon atoms, into contact with potassium hydroxide in an aqueous reaction medium in a stirred reactor equipped with at least one inlet for the reactants and with at least one outlet, to give the (hydro)fluoroolefin compound, which is separated from the reaction medium in the gaseous form, and potassium fluoride, (ii) bringing the potassium fluoride formed in (i) into contact in an aqueous medium with calcium hydroxide in a second reactor, to give potassium hydroxide and to precipitate calcium fluoride, (iii) separating the calcium fluoride precipitated in stage (ii) from the reaction medium and (iv) optionally recycling the reaction medium to stage (i) after optional adjustment of the concentration of potassium hydroxide, characterized in that the potassium hydroxide represents, in the reaction medium of stage (ii), between 10 and 35% by weight, with respect to the weight of the water and potassium hydroxide mixture of the medium.

The present invention thus makes it possible to obtain an advantageous process as, on the one hand, potassium hydroxide is more reactive than calcium hydroxide in the dehydrofluorination reaction and, on the other hand, the conversion of the calcium hydroxide to give calcium fluoride, a by-product which can be recovered in value, is high.

The Applicant Company has observed that the process according to the present invention makes it possible to obtain a mean size at 50% by weight of the particle size distribution of calcium fluoride crystals of greater than 10 µm, indeed even of greater than 20 µm and more particularly of between 20 and 60 µm and thus to facilitate the washing and filtration operations and the recycling of the potassium hydroxide.

The reaction medium of stage (i) is stirred so as to provide for dispersion of the gas in the liquid medium.

The process according to the present invention preferably provides a (hydro)fluoroolefin compound comprising three carbon atoms, advantageously a (hydro)fluoroolefin compound represented by the formula (I)

$$CF_3CY=CX_nH_p \qquad (I)$$

in which Y represents a hydrogen atom or a halogen atom chosen from fluorine, chlorine, bromine or iodine, X represents a halogen atom chosen from fluorine, chlorine, bromine or iodine, and n and p are integers and can independently take the value zero, 1 or 2, provided that (n+p)=2, by bringing a compound of formula $CF_3CYRCR'X_nH_p$, in which X, Y, n and p have the same meanings as in the formula (I) and R represents a fluorine atom when R' represents a hydrogen atom or R represents a hydrogen atom when R' represents a fluorine atom, into contact with potassium hydroxide in stage (i).

The present invention is very particularly suited to the manufacture of a compound of formula (Ia)

$$CF_3—CF=CHZ \qquad (Ia)$$

in which Z represents a hydrogen atom or a fluorine atom, starting from a compound of formula $CF_3CFRCHR'Z$ in which Z has the same meanings as in the formula (Ia) and R represents a fluorine atom when R' represents a hydrogen atom or R represents a hydrogen atom when R' represents a fluorine atom.

Thus, 2,3,3,3-tetrafluoropropene can be obtained by dehydrofluorination of 1,1,1,2,3-pentafluoropropane with KOH and/or 1,2,3,3,3-pentafluoropropene can be obtained by dehydrofluorination of 1,1,1,2,3,3-hexafluoropropane with KOH in stage (i). The 1,2,3,3,3-pentafluoropropene can be in the form of the cis and/or trans isomer.

The present invention can additionally be used for the manufacture of 1,3,3,3-tetrafluoropropene by dehydrofluorination of 1,1,3,3,3-pentafluoropropane with KOH.

In stage (i) of the process according to the present invention, the potassium hydroxide can represent between 20 and 75% by weight, with respect to the weight of the water and KOH mixture present in the aqueous reaction medium, preferably between 55 and 70%. According to the content, the potassium hydroxide can be in the form of an aqueous solution or in the molten state.

Stage (i) is generally carried out at a temperature such that the water formed during the dehydrofluorination reaction is removed, in all or in part, from the reaction medium by entrainment of the gas stream comprising the (hydro)fluoroolefin compound resulting from the stirred reactor. This temperature is preferably between 80 and 180° C., advantageously between 125 and 180° C. and very particularly between 145 and 165° C.

The dehydrofluorination reaction of stage (i) can be carried out at atmospheric pressure but it is preferable to operate at a pressure greater than atmospheric pressure. Advantageously, this pressure is between 1.1 and 2.5 bar.

The reaction of stage (ii) can be carried out in a stirred reactor or a fluidized bed reactor by reacting calcium hydroxide, preferably in suspension in water, with the potassium fluoride originating from stage (i). The reaction temperature can vary within wide limits but, for economic reasons, it is preferably between 50 and 150° C., advantageously between 70 and 120° C. and more advantageously between 70 and 100° C.

When a calcium hydroxide suspension is used in stage (ii), the calcium hydroxide represents between 2 and 40% by weight, with respect to the weight of the suspension.

Advantageously, stage (ii) is fed with potassium fluoride via the reaction medium originating from stage (i) comprising water, potassium hydroxide and potassium fluoride. The potassium fluoride in stage (i) can be dissolved or in suspension. The potassium fluoride preferably represents between 4 and 45% by weight of the reaction medium from stage (i).

In the stage (ii), two mol of potassium fluoride react with one mol of calcium hydroxide to give one mol of potassium fluoride and two mol of potassium hydroxide. This generation of potassium hydroxide makes it possible to limit the optional need to reconcentrate and thus reduces the addition of potassium hydroxide in the process.

It is possible to provide a stage of dilution of the reaction medium between stage (i) and stage (ii).

The calcium fluoride precipitated in stage (ii) is separated from the reaction medium, for example by filtration and/or settling. A settling stage can be provided prior to the filtration. The calcium fluoride thus separated is subsequently washed with water.

During the settling stage, it is possible to provide for the recycling of a portion of the concentrated calcium fluoride suspension to stage (ii). Advantageously, the level of calcium fluoride solids present in the reaction medium of stage (ii) is between 2 and 30% by weight.

After separation of the calcium fluoride, the reaction medium, with or without aqueous liquors from washing the calcium fluoride, can be recycled to stage (i), after optional adjustment of the potassium hydroxide content.

It can be advantageous to use an inert gas in the dehydrofluorination stage.

The process according to the invention has the advantage of resulting in high yields, even in the absence of phase transfer catalyst and/or organic solvent.

The present invention also comprises the combinations of the preferred forms, whatever the embodiment.

EXPERIMENTAL PART

Example 1

1 kg of 50% by weight potassium hydroxide comprising 9% by weight of KF is introduced into a reactor and heated to 100° C. 109 g of $Ca(OH)_2$ assaying 96% by weight (major impurity being $CaCO_3$) are subsequently added with stirring at 500 revolutions/min. After reacting for one hour, the suspension is withdrawn. The level of solids is 3.5% by weight and the composition by weight of the solids is as follows:
$CaF_2$: 60%
$Ca(OH)_2$: 36%
$CaCO_3$: 4%

Example 2

The operation is carried out as in Example 1, except that 1 kg of 25% by weight potassium hydroxide is introduced.

The composition by weight of the solids, after reacting for one hour, is as follows:
$CaF_2$: 95%
$Ca(OH)_2$: 1%
$CaCO_3$: 4%.

Example 3

A reactor maintained at 100° C. and stirred at 500 rev/min is fed continuously with a potassium hydroxide solution resulting from the dehydrofluorination stage and assaying, after dilution, 28% by weight of potassium hydroxide and 6% by weight of KF. The Ca(OH)$_2$ suspension feeding the reactor assays 20% by weight. The residence time in the reactor is approximately 1 h.

The ability to be filtered of the suspension obtained after reaction is very good.

The level of solids of the suspension at the outlet of the reactor is 3.6% by weight.

The particle size of the calcium fluoride synthesized is 30 μm and its purity is greater than 85% by weight.

Example 4

FIG. 1 gives the diagram of an embodiment of the present invention. A stirred reactor (1), equipped with a heating/cooling device and a device for measuring the temperature of the reaction medium, which comprises a water and KOH mixture in which the KOH is present at 60% by weight in the water, is fed continuously with a solution of molten KOH (2), in which the KOH is present at 65% by weight in the water, and with 1,1,1,2,3,3-hexafluoropropane (3). The temperature is maintained at 150° C. and the pressure in the reactor is 1.2 bar absolute. The gaseous products exit from the reactor via an orifice (4) situated on the lid and the water present in the gas stream is removed by condensation (13).

The material exiting (5) from the reactor (1) is diluted in line with water (6) in order to obtain a KOH assay of 30%. This mixture is conveyed to the inlet of the reactor (7) and thus provides for the feeding of the reactor (7) with potassium fluoride, which can be in suspension in the aqueous medium. A suspension of 15% by weight of calcium hydroxide in water is introduced into the reactor (7) via the route (8). The reactor (7) is maintained at a temperature of between 70 and 80° C.

The outlet of the reactor (7) is connected to a filter (9), in order to separate the calcium fluoride from the reaction medium and then to wash it with water (10); the aqueous medium separated from the calcium fluoride is subsequently recycled to the reactor (1) after adjustment of the KOH concentration. The aqueous liquors from washing the calcium fluoride are recycled to the tank (16) for preparation of the suspension of calcium hydroxide in water.

The molten KOH mixture feeding the reactor (1) is prepared by evaporation (removal of water (15)) of a 50% by weight aqueous KOH solution (14) and of the aqueous solution originating from the filter (9).

At the outlet of the reactor (1), the degree of molar conversion of the 1,1,1,2,3,3-hexafluoropropane is greater than 98%. The selectivity for 1,1,1,2,3-pentafluoropropene is greater than 99%.

At the outlet of the reactor (7), the degree of molar conversion of the calcium hydroxide is greater than 85%.

Example 5

The operation is carried out at Example 4, except that the reactor (1) is fed continuously with 1,1,1,2,3-pentafluoropropane instead of 1,1,1,2,3,3-hexafluoropropane.

The stirred reactor (1) comprises a water and KOH mixture in which the KOH is present at 65% by weight in the water.

At the outlet of the reactor (1), the degree of molar conversion of the 1,1,1,2,3,-pentafluoropropane is greater than 98%. The selectivity for 1,1,1,2-tetrafluoropropene is greater than 99%.

Example 6

A reactor maintained at 80° C. and stirred at 500 rev/min is fed continuously with a potassium hydroxide solution resulting from the dehydrofluorination stage and assaying, after dilution, 32.8% by weight of potassium hydroxide and 9.7% by weight of KF. The Ca(OH)$_2$ suspension feeding the reactor assays 15% by weight. The residence time in the reactor is approximately 1 h.

The ability to be filtered of the suspension obtained after reaction is very good. The level of solids of the suspension at the outlet of the reactor is 3.6% by weight. The particle size of the calcium fluoride synthesized is 30 μm and its purity is greater than 85% by weight.

The invention claimed is:

1. A process for the continuous or semicontinuous manufacture of a (hydro)fluoroolefin compound comprising
   (i) bringing at least one compound comprising from three to six carbon atoms, at least two fluorine atoms and at least one hydrogen atom, provided that at least one hydrogen atom and one fluorine atom are situated on adjacent carbon atoms, into contact with potassium hydroxide in an aqueous reaction medium in a stirred reactor equipped with at least one inlet and with at least one outlet, to yield the (hydro)fluoroolefin compound and potassium fluoride, wherein the (hydro)fluoroolefin compound is separated from the reaction medium in the gaseous form,
   (ii) bringing the potassium fluoride formed in stage (i) into contact in an aqueous medium with calcium hydroxide in a second reactor to yield potassium hydroxide and calcium fluoride precipitate,
   (iii) separating the calcium fluoride precipitated in stage (ii) from the reaction medium in stage (ii), wherein potassium hydroxide present in the reaction medium of stage (ii) represents between 10 and 35% by weight, with respect to the weight of the water and potassium hydroxide mixture of the reaction medium; and
   (iv) optionally recycling the reaction medium from stage (ii) to stage (i) after optional adjustment of the concentration of potassium hydroxide.

2. The process according to claim 1, characterized in that the (hydro)fluoroolefin comprises a compound of formula (I)

$$CF_3CY=CX_nH_p \qquad (I)$$

in which Y represents a hydrogen atom or a halogen atom chosen from fluorine, chlorine, bromine or iodine, X represents a halogen atom chosen from fluorine, chlorine, bromine or iodine, and n and p are integers and can independently take the value zero, 1 or 2, provided that (n+p)=2, and said at least one compound comprises a compound of formula CF$_3$CYRCR'X$_n$H$_p$, where R represents a fluorine atom when R' represents a hydrogen atom or R represents a hydrogen atom when R' represents a fluorine atom.

3. The process according to claim 1, characterized in that the (hydro)fluoroolefin comprises a compound of formula (Ia)

$$CF_3\text{---}CF=CHZ \qquad (Ia)$$

in which Z represents a hydrogen atom or a fluorine atom, and said at least one compound comprises a compound of formula CF$_3$CFRCHR'Z, where R represents a fluorine atom when R' represents a hydrogen atom or R represents a hydrogen atom when R' represents a fluorine atom.

4. The process according to claim 1, characterized in that said (hydro)fluoroolefin comprises 2,3,3,3-tetrafluoropropene and said at least one compound comprises 1,1,1,2,3-pentafluoropropane and/or said (hydro)fluoroolefin comprises 1,2,3,3,3-pentafluoropropene and said at least one compound comprises 1,1,1,2,3,3 hexafluoropropane.

5. The process according to claim 1, characterized in that the potassium hydroxide represent between 20 and 75% by weight, with respect to the weight of the water and KOH mixture present in the aqueous reaction medium of stage (i).

6. The process according to claim 1, characterized in that the temperature at which stage (i) is carried out is between 80 and 180° C.

7. The process according to claim 1, characterized in that the temperature of stage (ii) is between 50 and 150° C.

8. The process according to claim 1, characterized in that stage (ii) is fed with potassium fluoride via the reaction medium originating from stage (i).

9. The process according to claim 1, characterized in that the potassium fluoride represents between 4 and 45% by weight of the reaction medium from stage (i).

10. The process according to claim 8, further characterized in that water is added to the reaction medium of stage (ii).

11. The process according to claim 1, characterized in that the calcium fluoride in stage (iii) is filtered out after an optional settling stage.

12. The process according to claim 11, characterized in that, during settling, a portion of the concentrated calcium fluoride suspension is recycled to stage (ii).

13. The process according to claim 1, characterized in that said (hydro)fluoroolefin comprises 1,2,3,3,3-pentafluoropropene and said at least one compound comprises 1,1,1,2,3,3-hexafluoropropane.

14. The process according claim 1, characterized in that the potassium hydroxide represents between 55 and 70% by weight, with respect to the weight of the water and KOH mixture.

15. The process according to claim 1, characterized in that the temperature at which stage (i) is carried out is between 125 and 180° C.

16. The process according to claim 1, characterized in that the temperature at which stage (i) is carried out is between 145 and 165° C.

17. The process according to claim 1, characterized in that the temperature of stage (ii) is between 70 and 120° C.

18. The process according to claim 1, characterized in that the temperature of stage (ii) is between 70 and 100° C.

* * * * *